(12) United States Patent  
Arevalo

(10) Patent No.: US 8,784,918 B2  
(45) Date of Patent: Jul. 22, 2014

(54) SYSTEMS AND METHODS FOR PROCESSING COMESTIBLES

(75) Inventor: Pedro Armando Arevalo, Los Angeles, CA (US)

(73) Assignee: Lawrence Equipment, Inc., So. El Monte, CA (US)

( * ) Notice: Subject to any disclaimer, the term of this patent is extended or adjusted under 35 U.S.C. 154(b) by 549 days.

(21) Appl. No.: 13/089,876

(22) Filed: Apr. 19, 2011

(65) Prior Publication Data

US 2012/0269935 A1  Oct. 25, 2012

(51) Int. Cl.  
*B07B 13/065*  (2006.01)

(52) U.S. Cl.  
USPC .......................................... 426/231; 198/605

(58) Field of Classification Search  
CPC ................. B07C 2501/0081; B07B 13/065  
USPC ................. 426/231; 198/605; 83/401, 932  
See application file for complete search history.

(56) References Cited

U.S. PATENT DOCUMENTS

| | | | | |
|---|---|---|---|---|
| 2,370,539 A | * | 2/1945 | Hodecker | 209/668 |
| 3,207,309 A | * | 9/1965 | Ernst | 209/624 |
| 3,561,373 A | * | 2/1971 | Sievert | 99/334 |
| 3,844,411 A | * | 10/1974 | Lewis | 209/539 |
| 4,156,508 A | * | 5/1979 | Kisielewski | 241/80 |
| 5,839,954 A | * | 11/1998 | Schloesser et al. | 460/45 |
| 5,887,729 A | * | 3/1999 | Sugiyama | 209/665 |
| 6,321,914 B1 | * | 11/2001 | Magnusson et al. | 209/665 |
| 6,361,307 B1 | * | 3/2002 | Bernhard et al. | 425/193 |
| 6,863,132 B2 | * | 3/2005 | Visser | 171/113 |
| 8,286,798 B2 | * | 10/2012 | Ricketts et al. | 209/138 |
| 2008/0283453 A1 | * | 11/2008 | Ragnarsson | 209/665 |

FOREIGN PATENT DOCUMENTS

DE  19945038 C1  * 12/2000

OTHER PUBLICATIONS

CasaHerrera, CH-51 Automated Inspection Systems, [Online], Retrieved from the Internet at http://www.casaherrera.com/machine-tortilla-flatbread-automated-inspection-systems on Nov. 9, 2010, 3 pages.

CasaHerrera, CH-51 Automated Inspection Systems, [Online], Retrieved from the Internet at http://www.casaherrera.com/managedocs/download.php?doc=brochure_vision_system_CH-51_Flour.pdf on Nov. 9, 2010, 2 pages. Dated Jan. 22, 2010.

PCT/US2009/042519 International Search Report and Written Opinion of International Searching Authority, ISA European Patent Office, mailed Apr. 27, 2010, 11 pages.

* cited by examiner

*Primary Examiner* — Steven Leff  
(74) *Attorney, Agent, or Firm* — Fish & Richardson P.C.

(57) ABSTRACT

In some implementations, a banded discharge removes or rejects comestibles from a production line when the comestibles have a diameter less than a minimum value. The banded discharge may include two or more support members and each pair of adjacent support members may be spaced apart a distance W. When a comestible with a diameter about the same as or less than the distance W moves onto the banded discharge, the banded discharge may remove the comestible from the production line. For example, the comestible may fall between two adjacent support members.

20 Claims, 9 Drawing Sheets

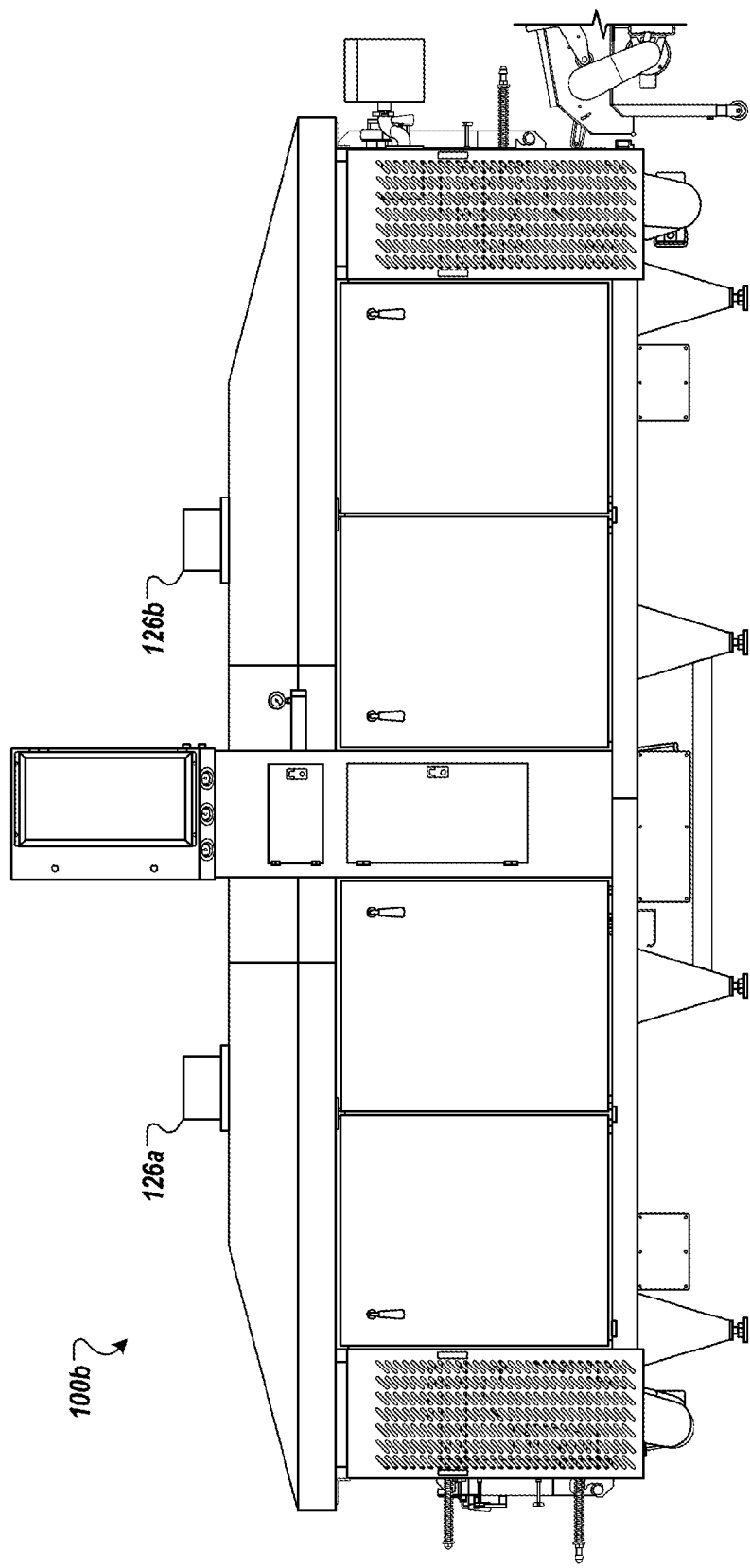

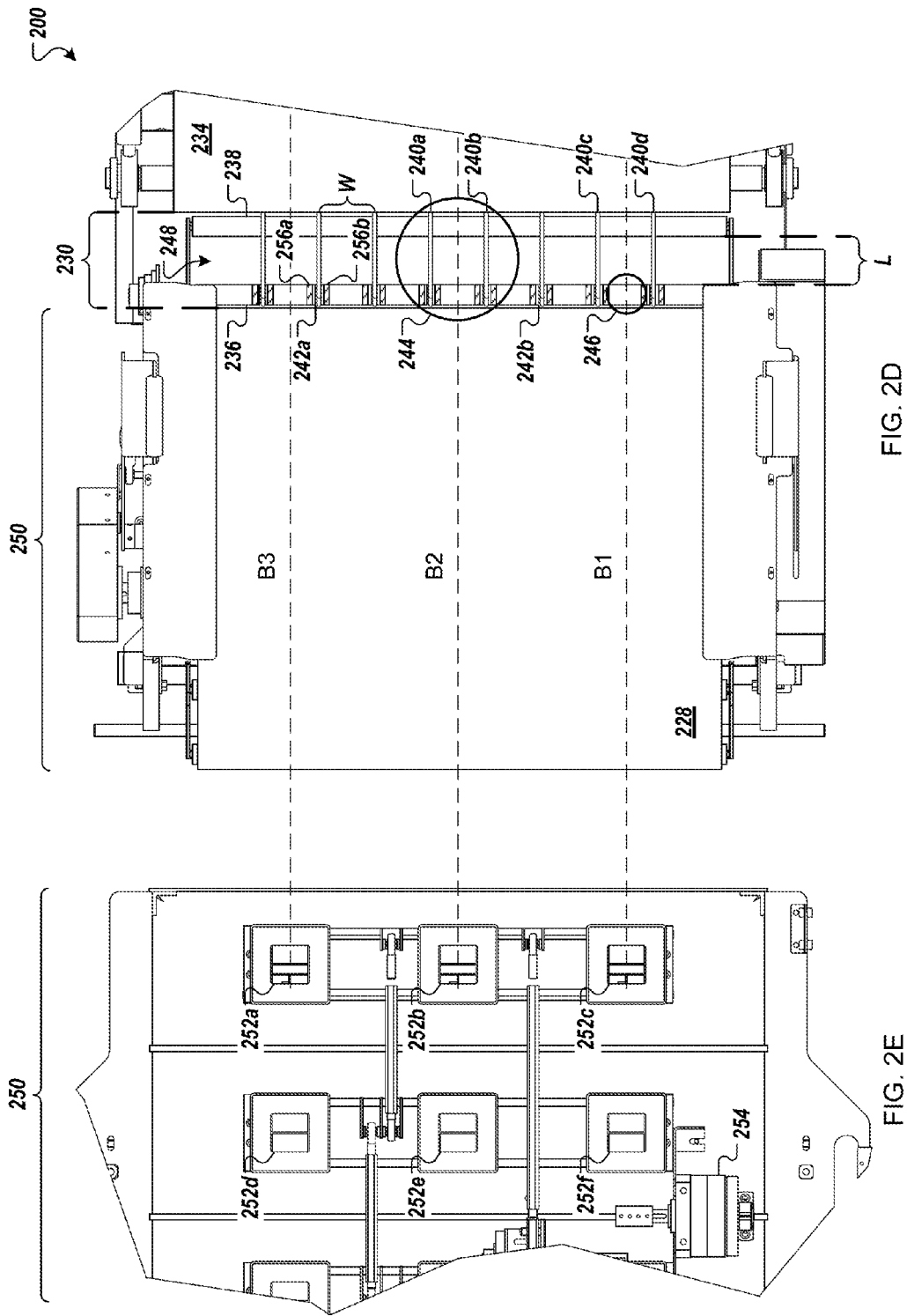

SYSTEMS AND METHODS FOR PROCESSING COMESTIBLES

BACKGROUND

Flatbread is made from flour, water, and salt and formed into flattened dough before baking. Some flatbreads include additional ingredients such as curry powder, black pepper, olive oil, or sesame oil. The thickness of the flattened dough can range from one thirty-second of an inch to over an inch thick.

Flatbreads are made by hand or with automated equipment. For example, a factory or a production line can be used to produce one or more types of flatbread to reduce the cost of making the bread. One automated method of forming flatbread includes pressing flatbread dough.

Factories can include different types of tools for the different stages in the production process, such as a mixer, an oven, and a cooler. Some production lines have a tool to form flatbread dough into a ball and another tool to flatten the dough before baking. The flattened dough has a circular shape and a specific thickness so the flatbread will have a desired thickness after baking.

For example, a pressing apparatus presses a ball of dough until the pressed dough ball has a certain diameter. After the pressure is released from the pressed dough ball, the diameter of the pressed dough ball sometimes decreases due to elasticity of the dough. Changes to different process parameters, such as a heating temperature during pressing and the ingredients in the dough, sometimes have an effect on the diameter of the dough after pressing is completed. For example, a higher pressing temperature can help a pressed dough ball retain its shape.

SUMMARY

In some implementations, a banded discharge removes or rejects comestibles from a production line when the comestibles have a diameter less than a minimum value. The banded discharge may include two or more support members and each pair of adjacent support members may be spaced apart a distance W. When a comestible with a diameter about the same as or less than the distance W moves onto the banded discharge, the banded discharge may remove the comestible from the production line. For example, the comestible may fall between two adjacent support members.

In a preferred embodiment, the banded discharge rejects comestibles with a thickness greater than a predetermined thickness to prevent a jam in the production line. For example, the diameter and thickness of a comestible are inversely proportional. When the comestible has a diameter less than the distance W, the comestible may have a thickness greater than a predetermined thickness and may clog the production line.

In various implementations, the banded discharge includes two rollers that support and translate the support members. A distance between the two rollers is optionally less than a desired comestible diameter. For example, the distance between the two rollers may be about 2 inches less than the desired comestible diameter.

In various implementations, each of the support members may have a diamond cross section. In other implementations, each of the support members may have an inverted "V" cross section. Each of the support members may be manufactured from polyurethane. In certain implementations, each of the support members may be made form an elastomer. The hardness of each of the support members may be between about 50 to about 100 Durometer.

A desired diameter of the comestible may be specified by a production line process recipe. For example, the recipe may include a range for the desired diameter of comestibles pressed in the production line. The support members in the banded discharge may be positioned based on a selected recipe or input recipe parameters. The distance between the rollers that support the support members and the lengths of the support members may be determined based on the production line recipe.

In some implementations, the banded discharge can be positioned between two additional conveyors. In other implementations, the banded discharge can be located between a conveyor and an apparatus (e.g., a pressing apparatus).

The details of one or more implementations are set forth in the accompanying drawing and description below. Other features, objects, and advantages will be apparent from the description and drawings, and from the claims.

DESCRIPTION OF DRAWINGS

FIGS. 1A-D illustrate an example of part of a production line.

FIGS. 2A-E illustrate an example of a transfer system.

Like reference symbols in various drawing indicate like elements.

DETAILED DESCRIPTION OF ILLUSTRATIVE IMPLEMENTATIONS

A comestible or flatbread production line includes a dough pressing station that flattens a ball of dough to a desired diameter before cooking. Sometimes, the dough pressing station does not press every ball of dough that moves through the production line. For example, if a ball of dough is misaligned with the production line (e.g., with the pressing station), malformed, or missing, one or more balls of dough may not be correctly formed (e.g., sufficiently pressed, or have a correct shape) at the pressing station.

The flatbread production line includes a banded discharge that removes or rejects balls of dough that have a diameter equal to or less than a predetermined value from the production line to prevent the balls of dough from causing a jam or otherwise stopping the production line. For example, the banded discharge removes incorrectly formed balls of dough that have a diameter less than the predetermined value from the production line.

The banded discharge includes two or more transfer support members that support formed dough balls with a diameter greater than a predetermined value while allowing incorrectly formed balls of dough with a diameter equal to or less than the predetermined value to fall between adjacent transfer belts. The incorrectly formed balls of dough are transferred away from the banded discharge after falling through the aperture between adjacent transfer belts.

The location of the banded discharge is determined based on the specific equipment used in the production line. For example, if the production line includes an oven with multiple conveyors that transfer a pressed dough ball between the multiple conveyors, a banded discharge is placed before the oven. Alternatively, if the oven includes only a single conveyor and a cooler includes multiple conveyors, a banded discharge is placed before the cooler and after the oven.

In some implementations, a banded discharge reduces the down time of the production line. For example, the banded discharge eliminates or reduces the number of jams created by incorrectly formed balls of dough and the need to clear the jams. Incorrectly formed balls of dough can include balls of dough that are not pressed at a pressing station, balls of dough that do not complete a pressing process, or any other shape or size of dough ball where a horizontal axis of the dough ball is less than a predetermined recipe value (e.g., a width W).

Figure 1A:
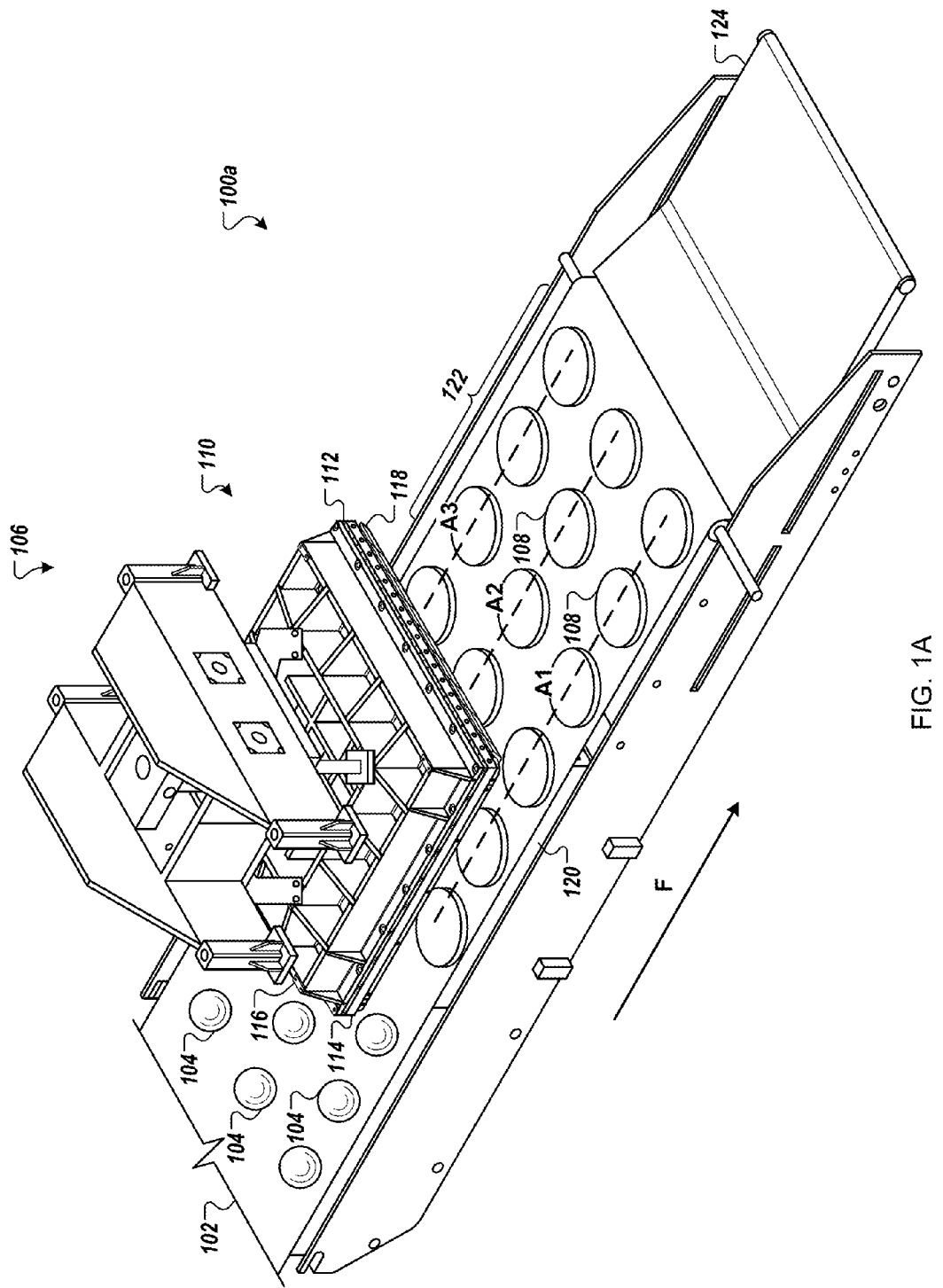

FIG. 1A is an example of a dough pressing apparatus 100a. The dough pressing apparatus 100a includes a conveyor 102 that receives one or more balls of dough 104 (e.g., with a width between about 1.5 to about 4.0 inches). The balls of dough 104 are placed on the conveyor 102 by a loading station or another conveyor (not shown). The temperature of the conveyor 102 is the same as the ambient environment around the dough pressing apparatus 100a.

A pattern of dough balls is placed on the conveyor 102 so that each of the individual balls of dough aligns with a pressing surface of a pressing station 106. For example, three longitudinal columns of the balls of dough 104 are placed on the conveyor 102 to align approximately with three longitudinal axes A1-3 of the dough pressing apparatus 100a.

The conveyor 102 moves the pattern of dough balls into the pressing station 106, which presses the balls of dough 104 and forms a plurality of pressed dough balls 108. In some implementations, the pressure used at the pressing station 106 is adjusted based on the actual diameters of the pressed dough balls 108 if a number of the pressed dough balls 108 have a diameter that is smaller or larger than the desired diameter. For example, if there are nine balls of dough in a press cycle, and six of the pressed dough balls 108 have an actual diameter that is smaller than the desired diameter, the pressure used by the pressing station can be increased so that the diameters of the pressed dough balls 108 increases.

In certain implementations, some of the balls of dough 104 are not pressed or are not sufficiently pressed in order to prevent the ball of dough from creating a jam in a production line housing the dough pressing apparatus 100a. For example, if a loading station places a pattern of dough balls on the conveyor 102 that is missing some of the dough balls in the pattern, the pressing station 106 does not press the pattern of dough balls. Alternatively, the pressing station 106 does not completely press a pattern of dough balls according to recipe specifications when a dough ball is missing from the pattern of dough balls. In another example, one or more of the balls of dough 104 in the pattern may be malformed or smaller than a recipe size required for the balls of dough 104.

In one example, pressing a pattern of dough balls where one or more of the dough balls is missing or incorrectly formed may create an asymmetrical load on the frame of the pressing station 106. In some implementations, the pressing station 106 does not press or completely press the pattern of dough balls in order to prevent the asymmetrical load on the frame of the pressing station 106, which may cause extra wear or damage to the pressing station 106 and/or the conveyor 102.

In some implementations, the conveyor 102 moves one or more non-pressed or non-formed dough balls (e.g., the balls of dough 104) past the pressing station 106 before the non-pressed dough balls are pressed at the pressing station 106. For example, another conveyor (not shown) feeds the balls of dough 104 onto the conveyor 102 and the conveyor 102 moves one or more of the balls of dough 104 past the pressing station 106. In one example, the conveyor 102 moves one or more latitudinal rows of the balls of dough 104 past the pressing station 106 while aligning balls of dough with the pressing station 106 (e.g., because of a missing or incorrectly sized ball of dough).

The pressing station 106 optionally includes one or more sensors (e.g., a photo eye) which detect a missing or incorrectly formed dough ball. When one of the sensors detects a missing or incorrectly formed dough ball, a controller can provide a signal to the pressing station 106 so that the pressing station does not press or completely press the pattern of dough balls.

The pressing station 106 includes an upper pressing platen 110 that applies pressure downward on the balls of dough 104. The upper pressing platen 110 includes an upper insulator 112, an upper pressing plate 114, and an upper portion 116. The upper insulator 112 and the upper pressing plate 114 are mounted to the upper portion 116 with non-conductive bolts.

The upper insulator 112 provides thermal insulation so that heat from the upper pressing plate 114 does not pass into the upper portion 116 of the upper pressing platen 110. The upper insulator 112 is made from thermalate, such as Thermalate® H330 manufactured by Haysite. The upper insulator 112 has a maximum service temperature between about 500 to about 1000° F., preferably between about 500 to about 850° F., more preferably between about 550 to about 800° F.

The upper insulator 112 has a compressive strength between about 17,000 to about 49,000 PSI, preferably between about 26,200 to about 49,000 PSI, more preferably between about 26,200 to about 44,000 PSI. In some implementations, the upper insulator 112 is composed of glastherm, such as Glastherm® HT or Cogetherm® manufactured by Glastic Corporation.

The upper insulator 112 and the upper pressing plate 114 are square with a length and a width between about 12 to about 72 inches, preferably between about 15 to about 60 inches. In certain implementations, the upper insulator 112 has a rectangular shape. In some implementations, the upper insulator 112 and the upper pressing plate are square with a width and length between about 37 to about 42 inches. The upper insulator 112 has a thickness between about 0.5 to about 2 inches, preferably between about 0.75 to about 1.75 inches, more preferably about 0.75 inches. The size and shape of the upper insulator 112 and/or the upper pressing plate 114 is determined by the production line housing the dough pressing apparatus 100a and the process recipes used in the production line.

The upper pressing plate 114 includes one or more heating channels (not shown). The heating channels include one or more heating elements that increase the temperature of the upper pressing plate 114 during processing. In some implementations, a heating fluid, such as a liquid or a gas, flows through the heating channels in order to heat the upper pressing plate. For example, Argon gas passes through the heating channels and heats the upper pressing plate 114 to a temperature between about 150 to about 750° F., preferably between about 250 to about 550° F., more preferably between about 300 to about 400° F. The temperature of the upper pressing plate 114 is determined based on a process recipe used by the dough pressing apparatus 100a.

The thickness of the upper pressing plate 114 is selected based on the pressure applied to the balls of dough 104 and the temperature required to heat the balls of dough 104 during processing. For example, the upper pressing plate 114 has a thickness between about 1 to about 5 inches, preferably between about 1.5 to about 3 inches. For example, the finished thickness of the upper pressing plate 114 can be about 2.974 inches.

In some implementations, the thickness of the upper pressing plate 114 is selected based on the composition of the upper pressing plate 114. For example, when the upper pressing plate 114 is made from graphene, the upper pressing plate 114 is thinner than if the upper pressing plate 114 was made from gold.

The upper pressing plate 114 is made from a material with a high thermal conductivity. The upper pressing plate 114 has a thermal conductivity between about 5 to about 5500 W/(m*K), preferably between about 15 to about 2500 W/(m*K), more preferably between about 30 to about 500 W/(m*K). The thermal conductivity of the upper pressing plate 114 can be selected based on the process recipes used in the dough pressing apparatus 100a, the composition of the upper pressing plate 114, and/or a desired efficiency of the upper pressing plate 114.

In some implementations, the composition of the upper pressing plate 114 is selected based on the resistance of the material to wear or scratches. For example, stainless steel is used to increase hardness (e.g., durability) and corrosion resistance of the upper pressing plate 114. The increased hardness of stainless steel decreases scratches and dents made to the upper pressing plate 114.

In some implementations, the upper pressing plate 114 is manufactured from aluminum or an aluminum alloy in order to have high wear resistance, a light mass, and a reduced heating time (e.g., based on a thermal conductivity of about 120 to about 237 W/(m*K)). The upper pressing plate 114 can be made from ceramic material in order to withstand high processing temperatures without deforming (e.g., up to about 3,000° F.) and have a high wear resistance. Brass can be used for the upper pressing plate 114 based on the low friction of brass materials and good thermal conductivity (e.g., about 109 W/(m*K)).

The upper pressing platen 110 includes a skin 118 that protects the bottom surface of the upper pressing plate 114 from wear caused by heat and/or pressure during processing of the balls of dough 104. The skin 118 is attached to the upper pressing platen 110 using vacuum suction. Alternatively, the skin 118 is attached to the upper pressing platen 110 using bolts or clamps.

A pressure between about 3 to about 70 PSI is applied to the upper pressing platen 110 to press a bottom surface of the skin 118 against the balls of dough 104, preferably between about 5 to about 65 PSI. In some implementations, a pressure between about 9 to about 50 PSI is applied to the upper pressing platen 110.

The pressing station 106 uses different pressures based on the desired diameter of the pressed dough balls 108. For example, a higher pressure (e.g., 48 PSI) is used to create pressed dough balls with a larger diameter (e.g., 12 inches) and a lower pressure (e.g., 13 PSI) is used to create pressed dough balls with a smaller diameter (e.g., 5 inches).

The diameter of the pressed dough balls 108 is inversely proportional to the thickness of the pressed dough balls 108. For example, increasing the diameter of a specific pressed dough ball decreases the thickness of the specific pressed dough ball. In one example, a ball of dough with a specific volume has a diameter of 10 inches and a thickness of ¼ inches, and a ball of dough with the same volume and an 8 inch diameter has a thickness of $25/64$ inches.

The pressing station 106 includes a lower pressing platen 120. The lower pressing platen 120 applies pressure to the balls of dough 104 from below during processing. For example, the lower pressing platen 120 supports the balls of dough 104 on the conveyor 102 while the upper pressing platen 110 presses down on the top surface of the balls of dough 104.

The lower pressing platen 120 includes a lower pressing plate, a lower insulator, and a lower portion (not shown) similar to the upper pressing plate 114, the upper insulator 112, and the upper portion 116 respectively. For example, both the lower pressing plate and the upper pressing plate 114 are manufactured from stainless steel.

In some implementations, the lower pressing plate has a lower temperature than the upper pressing plate 114 in order to reduce the likelihood that a ball of dough will stick to the skin 118 after being pressed. For example, the pressed dough balls 108 are more likely to stick to a cooler surface, so the temperature of the lower pressing plate is less than the temperature of the upper pressing plate 114 and the skin 118 so that the pressed dough balls 108 will rest on the conveyor 102 after processing instead of sticking to the skin 118 and lifting off the conveyor 102.

For example, the lower pressing plate has a temperature between about 150 to about 750° F., preferably between about 250 to about 550° F., more preferably between about 300 to about 400° F. In one example, when the upper pressing plate 114 has a temperature of around 350° F., the skin 118 has a temperature of around 340° F., and the lower pressing plate has a temperature of around 325° F.

The dough pressing apparatus 100a is configured to process different recipes for different types of dough, different sizes of dough, and/or different shapes of dough. For example, different recipes can have a different press cycle layout or pattern of dough balls, such as a square 2×2 to a square 8×8 layout or a rectangular 5×6 or 4×3 layout. When different press cycle layouts are used, the dough pressing apparatus 100a includes a number of longitudinal axes based on the number of longitudinal columns associated with the press cycle layout. For example, when using a 5×6 layout with 5 longitudinal columns, the dough pressing apparatus 100a includes five longitudinal axes A1-3.

After the pressed dough balls 108 are formed at the pressing station 106, the conveyor 102 moves the pressed dough balls 108 to a discharge station 122. In some implementations, the discharge station 122 includes a heater to parbake the pressed dough balls 108. For example, parbaking the pressed dough balls 108 at the discharge station allow the temperature of the lower pressing platen 120 to be reduced. In some implementations, forming the pressed dough balls 108 with a reduced temperature of the lower pressing platen 120 creates rounder pressed dough balls 108.

The pressed dough balls 108 are transferred from the discharge station 122 to an oven 100b, shown in FIG. 1B. For example, a conveyor 124 transfers the dough balls to the oven 100b from the discharge station 122.

The oven 100b includes an oven conveyor (not shown) that transfers the pressed dough balls 108 through the oven 100b during the cooking process. As the pressed dough balls 108 are conveyed through the oven 100b, the pressed dough balls 108 are cooked so that when the pressed dough balls 108 exit the oven 100b, the cooking process is complete. Alternatively, when the pressed dough balls 108 are removed from the oven 100b by the oven conveyor, the pressed dough balls 108 proceed to another cooking process.

The oven 100b includes one or more gas heaters (not shown) to cook the pressed dough balls 108. The gas heaters increase heat control (e.g., heat uniformity) of the cooking process of the pressed dough balls 108. In certain implementations, when the oven 100b includes gas heaters, the gas heaters allow the oven 100b to adjust temperature more quickly. For example, when the production line is initially started the oven 100b heats up to a processing temperature more quickly using gas heaters. Alternatively, the oven 100b can use electric heaters to cook the pressed dough balls 108.

In various implementations, the oven 100b is a convection oven. A convection oven, for example, provides greater temperature uniformity during the cooking process. For example, the pressed dough balls 108 are cooked more evenly with an electric convection oven. Alternatively, the oven 100b is a gas convection oven.

In certain implementations, the oven 100b uses infrared heat to cook the pressed dough balls 108. In these implementations, using infrared heat can provide a better distribution of heat in the oven 100b and cook the pressed dough balls 108 more evenly throughout the dough ball. For example, the oven 100b can require fewer heating elements when using infrared heat. In one example, the middle of a pressed dough ball is cooked approximately the same amount as the edge of the pressed dough ball when using infrared heat.

In some implementations, the oven 100b includes a stack of conveyors with each adjacent conveyor running in opposite directions across the oven. As each of the pressed dough balls 108 reaches the end of one of the conveyors, the pressed dough balls 108 pass through a turnaround that flips the pressed dough balls 108 over and places the pressed dough balls 108 on the next conveyor down in the stack of conveyors. This allows both sides of the pressed dough balls 108 to be cooked as evenly as possible in the oven 100b.

In one example, when the oven 100b includes a stack of conveyors and uses infrared heat to cook the pressed dough balls, the number of heating elements needed in the oven 100b is reduced because the infrared heat is evenly distributed throughout the oven 100b. In various implementations, using infrared heat reduces the amount of time necessary to cook the pressed dough balls 108.

In certain implementations, the oven conveyor in the oven 100b is heated. Heating the oven conveyor, for example, can reduce the amount of time needed to cook the pressed dough balls 108 because the pressed dough balls 108 are cooked on both sides at the same time.

The oven 100b includes one or more vents 126a-b that exhaust gases and/or heat from the oven 100b and prevent the gases and/or heat from entering the factory housing the production line. For example, the vents 126a-b draw gases from oven 100b to prevent the gases from building up. The vents 126a-b bring fresh air into the oven 100b and/or the factory housing the production line to prevent a back draft of air caused by the exhaust of the gases and/or heat from the oven 100b. Additionally, the vents 126a-b can remove heat from the oven 100b as necessary during the cooking process.

Figure 1C:
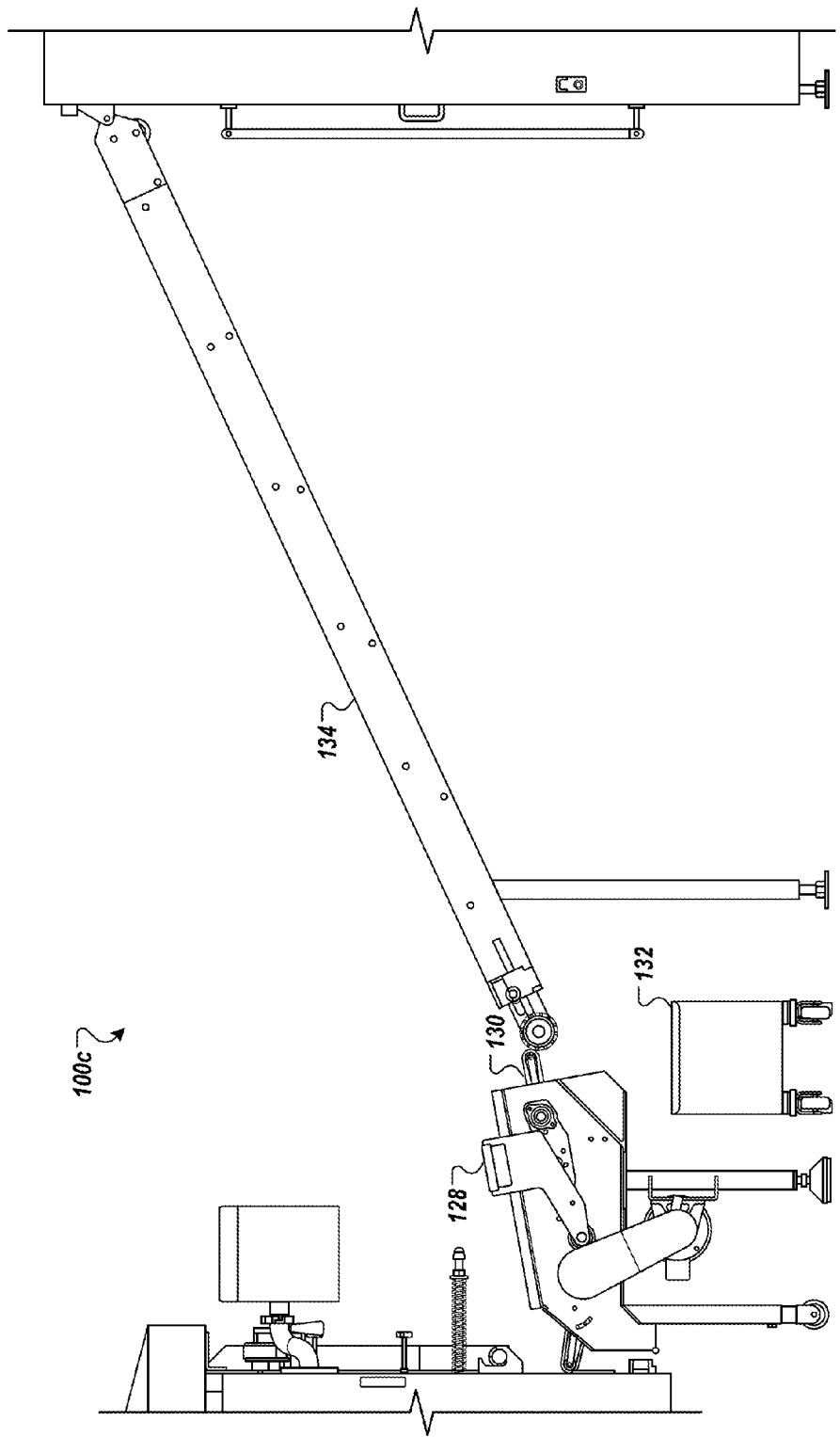
Figure 1D:
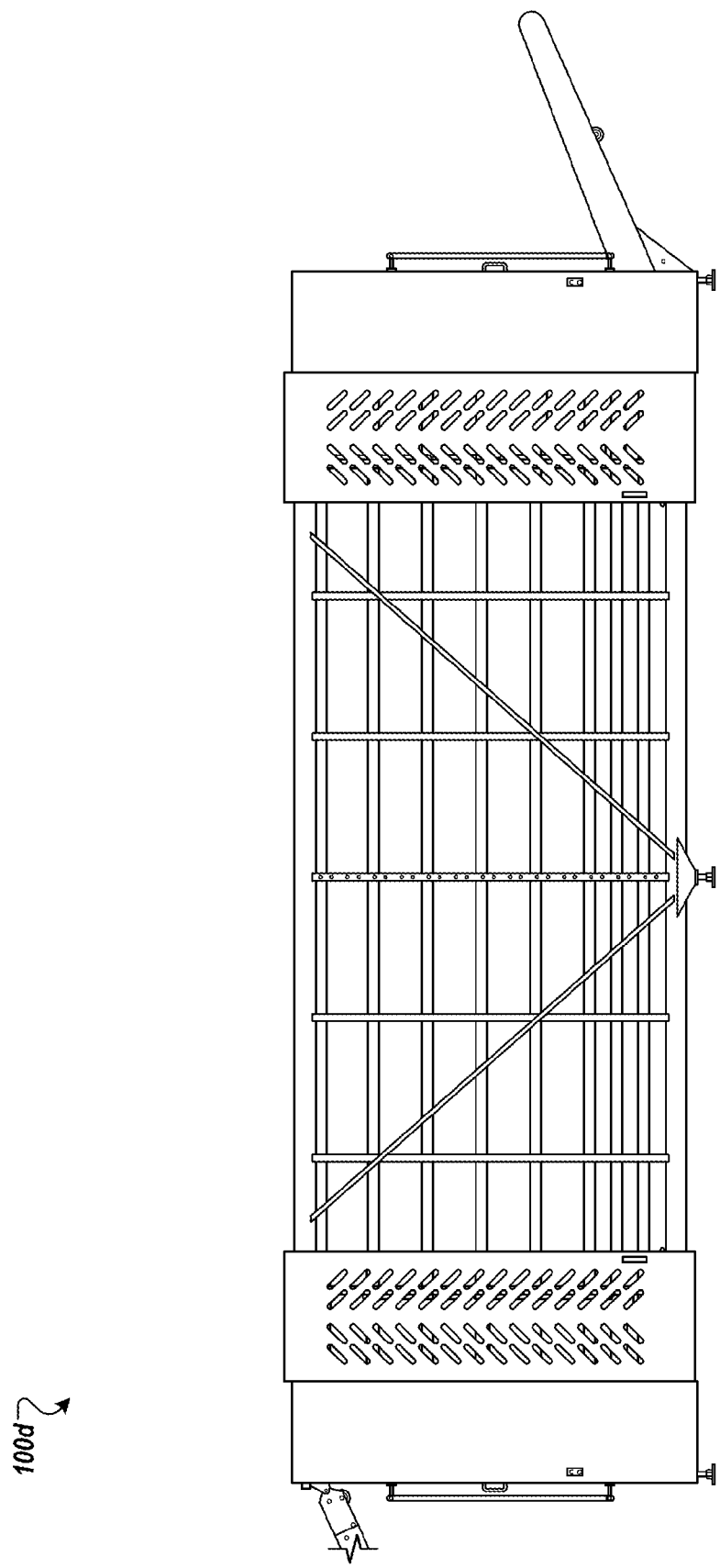

After cooking, the oven conveyor releases the pressed dough balls 108 onto a transfer system 100c, shown in FIG. 1C. The transfer system 100c moves the pressed dough balls 108 from the oven 100b to a cooler 100d, discussed in more detail below with reference to FIG. 1D.

The transfer system 100c includes an oven removal conveyor 128. The oven removal conveyor 128 transfers the pressed dough balls 108 to a banded oven discharge 130, described in more detail below with reference to FIGS. 2A-E.

The banded oven discharge 130 includes multiple support members that allow incorrectly formed dough balls to fall between adjacent bands and into a rejected product cart 132 for removal from the production line while the pressed dough balls 108 pass across the banded oven discharge 130. Once the rejected product cart 132 is full, the rejected product cart 132 is removed from the production line and another cart is placed below the banded oven discharge 130.

Alternatively, a conveyor located beneath the banded oven discharge 130 removes incorrectly formed dough balls from the production line area. For example, the conveyor transfers the incorrectly formed dough balls to another area in the factory housing the production line.

The banded oven discharge 130 transfers the pressed dough balls 108 from the oven removal conveyor 128 to a cooling rack input conveyor 134. The cooling rack input conveyor 134 transfers the pressed dough balls 108 into a cooler 100d, shown in FIG. 1D.

The cooler 100d includes multiple cooling conveyors (not shown) that transport the pressed dough balls 108 through the cooler 100d. As the pressed dough balls 108 move through the cooler 100d, air moving across the surfaces of the pressed dough balls 108 cools the pressed dough balls 108 to a reduced temperature.

For example, the pressed dough balls 108 have a temperature close to 200° F. when entering the cooler 100d. One or more fans move air from the environment outside of the cooler 100d (e.g., at an ambient temperature between about 65 to about 80° F., preferably between about 70 to about 75° F., more preferably about 72° F.) across the cooling conveyors and the pressed dough balls. As the air passes across the pressed dough balls 108, heat is removed from the pressed dough balls 108 and the pressed dough balls 108 are cooled. When the pressed dough balls 108 exit the cooler 100d, the pressed dough balls 108 are at a temperature close to the ambient temperature of the environment outside of the cooler 100d and can be packaged for shipment.

In some implementations, when the cooling conveyors are manufactured from a conductive material, the cooling conveyors reduce the temperature of the pressed dough balls 108. For example, heat from the pressed dough balls 108 dissipates into the cooling conveyors as the pressed dough balls 108 are transferred through the cooler 100d. As air from the ambient environment blows across the cooling conveyors, some of the heat is removed from the cooling conveyors, reducing the temperature of the cooling conveyors and another cycle of the cooling process begins.

In certain implementations, the cooling conveyors are cooled directly by the cooler 100d. For example, the cooler 100d includes a freezer that cools the cooling conveyors and provides indirect cooling to the pressed dough balls 108. In one example, the cooling conveyors are directly cooled by a refrigerant and the contact between the pressed dough balls 108 and the cooling conveyors as the pressed dough balls 108 move through the cooler 100d reduces the temperature of the pressed dough balls 108.

The multiple cooling conveyors in the cooler 100d are stacked above each other in the vertical direction (e.g., forming a multi-tier conveyor) and each of the conveyors transfers the pressed dough balls 108 in a different direction from the other conveyors adjacent to the conveyor.

The cooler 100d includes at least three conveyors in a multi-tier conveyor stack. In some implementations, the cooler 100d includes between seven and nineteen cooling conveyors. In another implementation, the cooler 100d includes between nine and twenty-one cooling conveyors, preferably between thirteen and seventeen cooling conveyors.

The number of cooling conveyors included in the cooler 100d can be determined based on the baking temperature of the pressed dough balls 108. For example, when the pressed dough balls 108 are baked at a higher temperature, the cooler 100d includes more cooling conveyors than when the pressed dough balls 108 are baked at a lower temperature. The number of cooling conveyors in the cooler 100d can be determined based on the maximum or highest allowable temperature of the oven 100b.

For example, the number and/or length of the cooling conveyors determines the length of time that the pressed dough balls 108 are in the cooler 100d and the change in temperature of the pressed dough balls 108. Additionally, the specific cooling methods used to reduce the temperature of the pressed dough balls 108 affect the number and/or length of the cooling conveyors.

In some implementations, the alignment of the pressed dough balls 108 as the pressed dough balls 108 move between adjacent conveyors is used to determine the number of cooling conveyors in the cooler 100d. For example, systems with more cooling conveyors may sometimes cause a pattern of dough balls to become misaligned so that the pattern no longer includes rows of dough balls that are in a uniform line (e.g., along a latitudinal axis perpendicular to the longitudinal axes A1-3) compared to a system with fewer cooling conveyors.

In one example, the cooler 100d includes thirteen cooling conveyors for cooling the pressed dough balls 108 to reduced or ambient temperature. A first conveyor in the cooler 100d transfers the pressed dough balls 108 from the left of the cooler 100d to the right of the cooler 100d, and a second conveyor directly below the first conveyor transfers the pressed dough balls 108 from the right of the cooler 100d to the left of the cooler 100d.

A turnaround (not shown) connecting the first conveyor and the second conveyor moves the pressed dough balls 108 between the adjacent conveyors while flipping the pressed dough balls 108 over to increase the uniformity of cooling of the pressed dough balls 108. The cooler 100d includes a turnaround between each of the adjacent cooling conveyors to move the pressed dough balls 108 between the adjacent conveyors in the cooler 100d.

The banded oven discharge 130 removes the non-pressed dough balls from the production line before the non-pressed dough balls can become stuck in a turnaround and cause a jam in the cooler 100d. In some implementations, removing non-pressed, incorrectly formed, or small dough balls from the production line at the banded oven discharge reduces the down time of the production line.

In implementations where the oven 100b includes multiple conveyors, a banded discharge (e.g., the banded oven discharge 130 and the rejected product cart 132) is located in the production line between the dough pressing apparatus 100a and the oven 100b. For example, the pressed dough balls 108 are transferred to the banded discharge from the conveyor 124 before entering the oven 100b. In these implementations, the banded oven discharge 130 is not included in the production line after the oven 100b.

FIGS. 2A-E illustrate an example of a transfer system 200 (e.g., the transfer system 100c). The transfer system 200 includes an oven removal conveyor 228, which removes the balls of dough from an oven (e.g., the oven 100b). A banded oven discharge 230 (e.g., a conveyor) receives the balls of dough from the oven removal conveyor 228 and disposes of one or more non-pressed or incorrectly formed balls of dough into a rejected product cart 232, shown in FIG. 2A.

For example, a ball of dough that was not flattened at a pressing station (e.g., the pressing station 106) falls through the banded oven discharge 230 and into the rejected product cart 232. In another example, a ball of dough that was not sufficiently pressed at the pressing station drops into the rejected product cart 232. In this example, the pressing station stopped pressing the ball of dough before the diameter of the ball of dough was about the same as a desired recipe diameter (e.g., based on a current recipe for the production line). Because the diameter and thickness of the ball of dough are inversely proportional, when the ball of dough has a diameter less than the desired recipe diameter, the ball of dough may cause a jam in the production line depending on how much the ball of dough was pressed.

The banded oven discharge 230 transfers the pressed dough balls 108 from the oven removal conveyor 228 to a cooling rack input conveyor 234. For example, the banded oven discharge 230 transfers all dough balls that have a horizontal diameter greater than a minimum recipe value to the cooling rack input conveyor 234. Alternatively, all dough balls with a diameter greater than about 6 inches are transferred to the cooling rack input conveyor 234.

The rejected product cart 232 is periodically emptied to prevent dough balls from overflowing out of the rejected product cart 232. For example, the rejected product cart 232 includes a plurality of sensors that determine the remaining capacity of the rejected product cart 232. When one or more of the sensors determine that the rejected product cart 232 or a portion of the rejected product cart 232 is nearing or at maximum capacity, the rejected product cart 232 is removed from the transfer system 200 and another rejected product cart is placed below the banded oven discharge 230. For example, an operator of the production line receives an alert message indicating that the rejected product cart 232 should be exchanged with another cart.

Alternatively, the transfer system 200 includes a conveyor, which removes incorrectly formed balls of dough from the transfer system 200. For example, the conveyor is located below the banded oven discharge 230 and does not move until a sensor detects that a ball of dough is located on the conveyor. Upon detection, the conveyor activates and removes the ball of dough away from the transfer system 200 and the banded oven discharge 230.

Figure 2A:
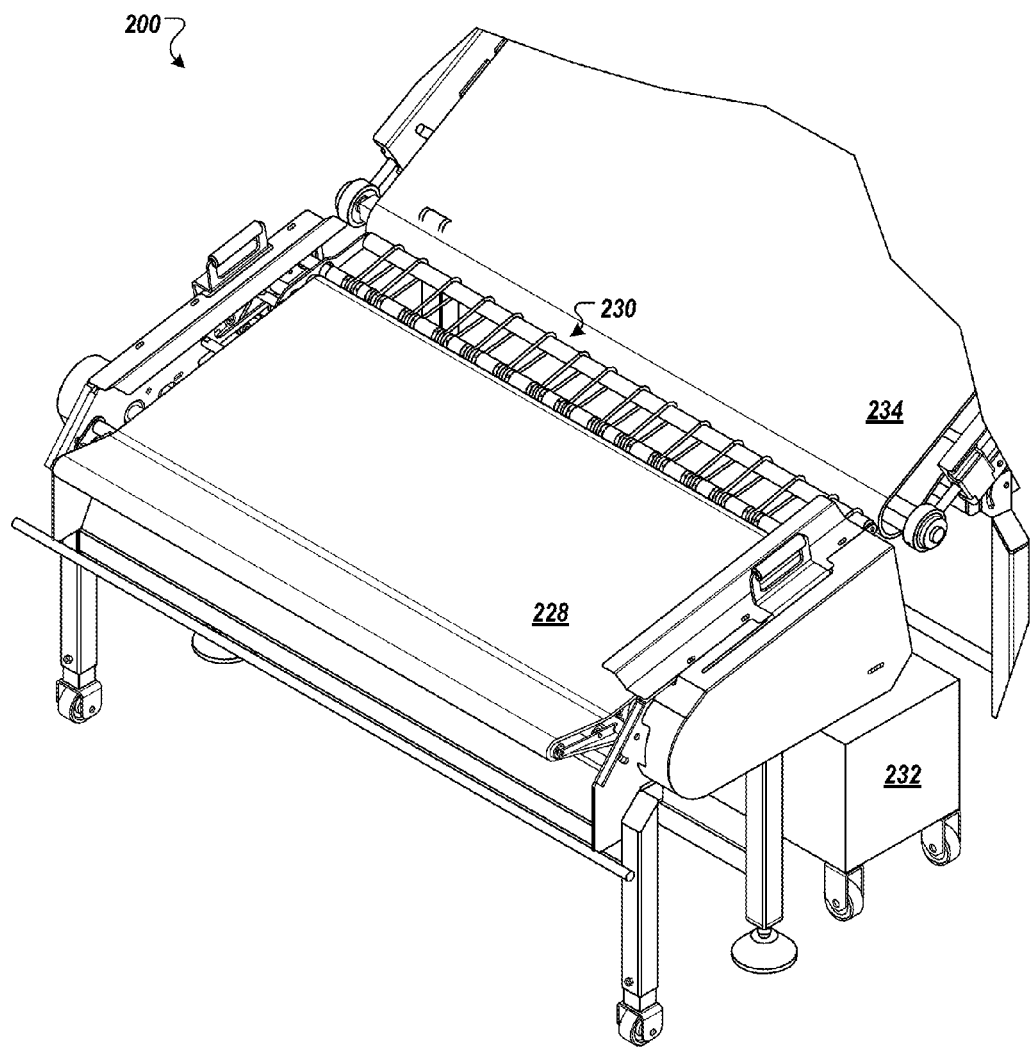
Figures 2B, 2C:
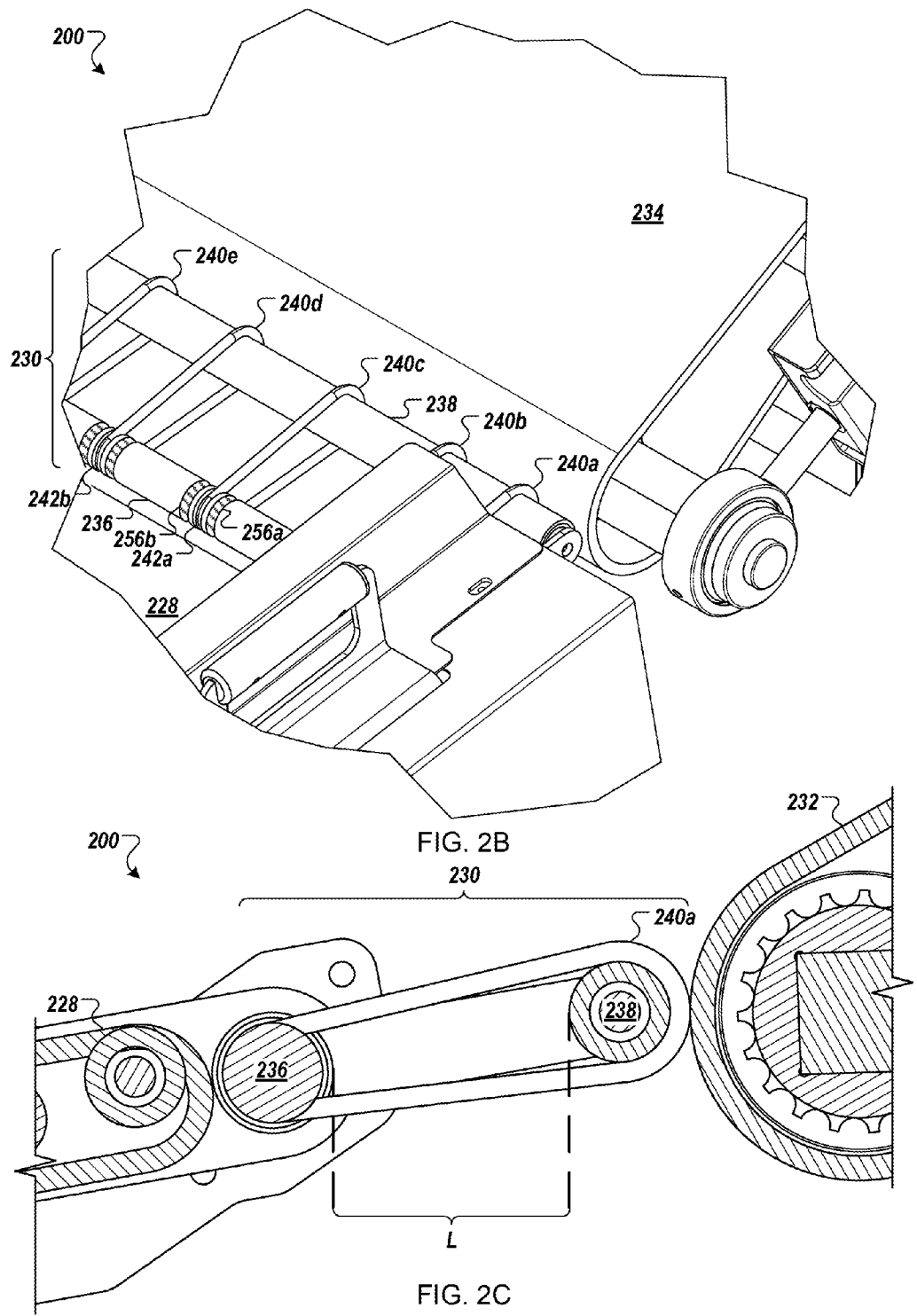

The banded oven discharge 230 includes a drive roller 236 and a passive roller 238, shown in FIG. 2B. The drive roller 236 moves a plurality of support members 240a-e (e.g., conveyors, transfer belts, or transfer bands), which support the pressed dough balls 108 as the pressed dough balls 108 pass over the banded oven discharge 230 in a longitudinal direction. The drive roller 236 is connected to a motor (not shown) which rotates the drive roller 236 in a clockwise direction, translating the support members 240a-e longitudinally through the banded oven discharge 230.

The passive roller 238 supports the ends of the support members 240a-e opposite the drive roller 236. The passive roller 238 is centered on a first horizontal plane different from a second horizontal plane at the center of the drive roller 236. For example, the first horizontal plane is above the second horizontal plane. Alternatively, the centers of the passive roller 238 and the drive roller 236 lie on the same plane.

In some implementations, the passive roller 238 is powered by a motor. For example, both the passive roller 238 and the drive roller 236 are connected to a motor (e.g., the same or different motors). Alternatively, the drive roller 236 is not connected to a motor and the passive roller 238 is connected to a motor. Selection of which rollers are powered and/or connected to a motor can be determined by the location of the banded oven discharge 230 in the production line.

The diameters of the drive roller 236 and the passive roller 238 are the same. For example, diameter of the rollers is between about 0.5 to about 3 inches, preferably between about 0.75 to about 2 inches, more preferably between about 1 to about 1.5 inches. Alternatively, the diameters of the drive roller 236 and the passive roller 238 are different. For example, the drive roller 236 has a diameter of 0.75 inches and the passive roller 238 has a diameter of 1.0 inch.

In certain implementations, the diameters of the drive roller 236 and/or the passive roller 238 are associated with the width of the oven removal conveyor 228 and/or the width of the cooling rack input conveyor 234. For example, the diameter of the drive roller 236 is larger when the width of the oven removal conveyor 228 is about 60 inches wide compared to when the width of the oven removal conveyor 228 is about 37 inches wide.

In various implementations, the diameters of the rollers are selected based on the material used to manufacture each of the rollers and to prevent the rollers from bending. For example, the diameter of the drive roller 236 is selected so that the driver roller 236 is strong enough that the driver roller 236 does not bend. In one example, when the drive roller 236 bends, the driver roller 236 may inadvertently deflect one of the pressed dough balls 108 off of the banded oven discharge 230.

In some implementations, when the diameter of the drive roller 236 and/or the passive roller 238 is smaller, the rollers provide better transfer for the pressed dough balls 108. For example, a smaller diameter for the drive roller 236 can reduce the possibility of a pressed dough ball becoming stuck on the driver roller 236 or between the drive roller 236 and one of the support members 240a-e.

The drive roller 236 and the passive roller 238 are manufactured from steel based on the structural robustness of steel. In one example, the rollers are manufactured from stainless steel based on the approval and/or certification of stainless steel for food processing.

In some implementations, one or both of the rollers are manufactured from aluminum in order to have a low mass and high wear resistance. Plastic can be used during the forming process of the drive roller 236 and/or the passive roller 238 based on the low mass of plastic and the ease of forming plastics in molds. Sometimes during the manufacturing process of one or both of the rollers wood is used. For example, one or more parts of the rollers and made from wood. In various implementations, the drive roller 236 and/or the passive roller 238 are made from a combination of materials.

In certain implementations, the drive roller 236 and/or the passive roller 238 include materials and/or compounds not included in the other roller. For example, the drive roller 236 is made from stainless steel and the passive roller 238 is made from steel and plastic.

The support members 240a-e are manufactured from polyurethane. For example, the support members 240a-e are belts which are made from polyurethane. In some implementations, the support members 240a-e are manufactured from an elastomer that can be stretched and has a memory to retract to the original size and shape of the support members 240a-e. For example, silicone is used to make the support members 240a-e based on the thermal stability, and low stick resistance of silicone. In various implementations, the support members 240a-e are Eagle polyurethane belting by Fenner Drives. In other implementations, the support members 240a-e are manufactured by DuraBelt, Inc. In some examples, the support members 240a-e are manufactured from food grade urethane.

In one example, the support members 240a-e are made from Viton, manufactured by DuPont Performance Elastomers L.L.C., based on the temperature range and good wear resistance of Viton. In some implementations, the support members 240a-e are manufactured from polyvinyl chloride for the flexibility of polyvinyl chloride. In certain implementations, Buna-N (or Nitrile) is used during manufacturing of the support members 240a-e based on the low cost and wear resistance of Buna-N.

The support members 240a-e have a circular cross section. The circular cross section is optionally hollow in the center to reduce the amount of material used to manufacture the support members 240a-e. In certain implementations, the support members 240a-e have a diamond cross section to decrease the amount of surface area that contacts balls of dough supported by the banded oven discharge. In some implementations, decreasing the amount of surface area that contacts the balls of dough reduces the likelihood that incorrectly formed products are transferred from the oven removal conveyor 228 to the cooling rack input conveyor 234 without falling into the rejected product cart 232.

In other implementations, the support members 240a-e have a "V" or inverted "V" cross section. The inverted "V" cross section can be selected to provide sufficient support to the pressed dough balls 108 wile reducing the amount of surface area of the support members 240a-e that contacts the pressed dough balls 108. In some implementations, the point of the inverted "V" is removed to increase the amount of surface area that contacts the pressed dough balls 108 while keeping the amount of surface area small.

In various implementations, the support members 240a-e have an oval cross section with the longer diameter in a vertical direction. Having an oval cross section decreases the amount of surface area contacting the balls of dough supported by the banded oven discharge while decreasing the amount the support members 240a-e sag when supporting a ball of dough. The support members 240a-e can have a half-oval or half-circular cross section. The base of the support members 240a-e (e.g., the flat surface) is firmly supported by the drive roller 236 while the half circle surface contacts the pressed dough balls 108.

In some implementations, the support members 240a-e are textured in order to improve contact between the support members 240a-e and balls of dough supported on the support members 240a-e. For example, using textured support members 240a-e can increase the speed of the pressed dough balls 108 as the pressed dough balls 108 move across the banded oven discharge 230 because the texturing helps prevent the pressed dough balls 108 from slipping.

The hardness of the support members 240a-e is between about 50 to about 100 Durometer, preferably between about 70 to about 90 Durometer, more preferably about 83 Durometer, for A or D type testing according to ASTM D2240 testing for softer or harder plastics. The hardness can be selected based on the diameter of the pressed dough balls 108. The hardness of the support members 240a-e can be selected to reduce the amount of wear on the support members 240a-e during processing.

The diameter of each of the support members 240a-e is between about 0.125 to about 0.5 inches, preferably between about 0.1875 to about 0.375 inches, more preferably between about 0.25 to about 0.3125 inches. For example, the diameter of the support members 240a-e is selected based on the diameter of the pressed dough balls 108 and/or the diameter of the balls of dough 104. In this example, the diameters of the support members 240a-e are selected in order to support the pressed dough balls 108 as the pressed dough balls 108 are transferred across the banded oven discharge 230. The diameter of the support members 240a-e is selected to reduce the possibility of one of the pressed dough balls 108 becoming stuck on one of the support members 240a-e or between one of the support members 240a-e and the drive roller 236.

In certain implementations, the diameter of the support members 240a-e is selected so that a minimum amount of power is required to drive the support members 240a-e. For example, when the support members 240a-e have a small diameter, less power is required to drive the support members 240a-e than if the support members 240a-e have a larger diameter and a larger mass.

In some implementations, the diameter of the support members 240a-e is selected so that the support members 240a-e easily conform to the drive roller 236 and/or the passive roller 238. In various implementations, the diameter of the support members 240a-e is selected to reduce the frequency and/or possibility of one of the support members 240a-e breaking.

In certain implementations, the drive roller 236 and/or the passive roller 238 include a plurality of grooves 242a-b corresponding with the support members 240a-e. For example, the drive roller 236 and the passive roller 238 include the grooves 242a-b to support the support members 240a-e and prevent the support members 240a-e from sliding in the latitudinal direction (i.e., to one of the sides of the banded oven discharge 230).

In these implementations, when the pressed dough balls 108 move across the banded oven discharge 230, the drive roller 236 and the passive roller 238 support the pressed dough balls 108. For example, the top surface the drive roller 236 is flush with the top surfaces of the support members 240a-e.

In one example, as a dough ball moves onto the banded oven discharge 130, the drive roller 236 supports the leading edge of the dough ball, and as the leading edge moves across the banded oven discharge 130, the passive roller 238 begins to support the leading edge. When a non-pressed or incorrectly formed ball of dough moves onto the banded oven discharge 130, for example, the leading edge of the incorrectly formed ball of dough contacts the drive roller 236 before the incorrectly formed ball of dough falls through the banded oven discharge 230 and into the rejected product cart 232 (e.g., the incorrectly formed ball of dough does not contact the passive roller 238).

In certain implementations, the shape of the grooves 242a-b corresponds with the shape of the support members 240a-e. For example, when the support members 240a-e have a circular cross section, the grooves 242a-b have an inverted "U" shape. In another example, when the support members 240a-e have an inverted "V" shape or a pentagonal shape, the grooves 242a-b are rectangular.

The width of the grooves 242a-b corresponds to the width of the support members 240a-e. For example, the width of the grooves 242a-b is slightly larger than the width of the support members 240a-e. The grooves 242a-b are between about 0.125 to about 0.5 inches wide, preferably between about 0.25 to about 0.32 inches wide, preferably about 0.278 inches wide.

Similarly, the height of the grooves 242a-b corresponds to the height of the support members 240a-e. For example, the height of the grooves 242a-b is between about 0.125 to about 0.5 inches, preferably between about 0.125 to about 0.375 inches, more preferably between about 0.125 to about 0.3125 inches. In some implementations, the height of the grooves 242a-b is less than the height of the support members 240a-e. For example, each of the grooves 242a-b has a height of 0.125 inches and each of the support members 240a-e has a height of 0.25 inches.

The gap L between the drive roller 236 and the passive roller 238, shown in FIG. 2C, has a minimum length of about 1.5 inches. The maximum length of the gap L between the drive roller 236 and the passive roller 238 is about 2 inches less than the diameter of the pressed dough balls 108. For example, the length of the gap is selected to be greater than the diameter of incorrectly formed balls of dough that may cause a jam in the production line and 2.0 inches less than the desired recipe diameter of the pressed dough balls 108.

In one example, when the diameter of the pressed dough balls 108 is about 10 inches, the length of the gap L is between about 5 to about 8.5 inches, preferably between about 6.5 to about 8 inches. In another example, when the diameter of the pressed dough balls 108 is about 6.0 inches, the length of the gap L is between about 1.5 to about 4 inches, preferably between about 2.5 to about 3.75 inches, more preferably between about 3 to about 3.5 inches.

The length of the support members 240a-e is determined based on the gap L between the drive roller 236 and the passive roller 238. For example, when the gap L has a longer length, the support members 240a-e have a longer length than compared to a smaller gap L corresponding with support members 240a-e with a shorter length.

The width W between two adjacent support members 240a-e (e.g., the support member 240a and the support member 240b), as shown in FIG. 2D, is selected so that balls of dough with a thickness greater than a predetermined thickness, which may cause a jam in the production line, are rejected by the banded oven discharge 230 and removed from the production line. For example, since the diameter of a ball of dough is inversely proportional to the thickness of the ball of dough, a process recipe includes a minimum value for the width W so that balls of dough with a thickness greater than the predetermined thickness are removed from the production line based on the diameter of the ball of dough.

The width W is between about 1 to about 6 inches, preferably between about 1.5 to about 5 inches, more preferably between about 2 to about 5 inches. The width W is selected so that the width W is about the same as or greater than the diameter of the incorrectly formed balls of dough and less than the diameter of the pressed dough balls 108.

For example, if a 3 inch diameter non-pressed ball of dough forms a 10.00 inch diameter pressed dough ball, the width W between adjacent support members 240a-e is between about 4 to about 6 inches, preferably between 4 to about 5 inches. In this example, an incorrectly formed ball of dough (e.g., with a diameter around 4 inches) will be rejected by the banded oven discharge 230 and fall between the support members 240a-e (e.g., with a width W of around 4 inches) while the pressed dough ball 244 is transferred across the banded oven discharge 230.

In some implementations, the width W between each pair of adjacent support members 240a-e is approximately the same. In other implementations, the width W between each pair of adjacent support members 240a-e is different. For example, the distance between adjacent support members is selected based on the recipe used by the production line.

The center of the balls of dough that the oven removal conveyor 228 transfers onto the banded oven discharge 230 (e.g., a pressed dough ball 244 and/or an incorrectly formed ball of dough 246) approximately aligns with one of three longitudinal axes B1-3 identified based on the press cycle layout.

When the press cycle layout used by the production line includes three longitudinal columns of balls of dough, the transfer system 200 includes the three longitudinal axes B1-3 corresponding with the three longitudinal axes A1-3 of the dough pressing apparatus 100a. If the recipe used by the product line changes and includes a change in the number of longitudinal columns of balls of dough, the number of axes in the transfer system 200 and the dough pressing apparatus 100a is adjusted to reflect the change.

In one example, when the recipe is changed from a 3×3 press cycle to a 5×5 press cycle, both the dough pressing apparatus 100a and the transfer system 200 include five longitudinal axes corresponding to a longitudinal column of the press cycle. When a ball of dough moves along a first axis in the dough pressing apparatus 100a (e.g., the axis A1) the ball of dough later moves along a corresponding first axis in the transfer system 200 (e.g., the axis B1) once the ball of dough is removed from the oven 100b and placed in the transfer system 200.

In this example, the location of the support members 240a-e is changed from the original configuration for the 3×3 press cycle. For example, the support members 240a-e are manually moved to correspond with the five axes associated with the new recipe so that each axis is centered between two adjacent support members. Alternatively, the support members 240a-e are automatically moved to new locations by the production line and/or a robot. For example, the drive roller 236 and the passive roller 238 do not have grooves and a robot arm automatically moves the support members 240a-e to new positions.

The three longitudinal axes B1-3 approximately align with the centers of a pair of adjacent support members. In one example, the longitudinal axis B2 is approximately centered between the support members 240a-b and the longitudinal axis B1 is approximately centered between the support members 240c-d.

Centering the longitudinal axes B1-3 between a pair of adjacent support members allows each of the pressed dough balls 108 to be supported by at least two of the support members 240a-e while incorrectly formed balls of dough are not supported by any of the support members 240a-e. In one example, the pressed dough ball 244 is supported by the support members 240a-b while the incorrectly formed ball of dough 246 falls through an aperture 248 between the drive roller 236 and the passive roller 238 and into the rejected product cart 232 (e.g., the incorrectly formed ball of dough 246 is not supported by either of the support members 240c-d).

In certain implementations, the pressed dough ball 244 is supported by at least two of the support members 240a-e to prevent the edges of the pressed dough ball 244 from becoming pinched between one of the support members 240a-e and the drive roller 236 or the passive roller 238. For example, if the pressed dough ball 244 is supported by a single support member, the pressed dough ball 244 may jam between the single support member and the passive roller 238.

In some implementations, an incorrectly formed ball of dough is supported by one of the support members 240a-e when moving onto the banded oven discharge 230. For example, the incorrectly formed ball of dough 246 is supported by the support member 240c. In this example, the incorrectly formed ball of dough 246 will fall off the support member 240c and into the rejected product cart 232 because the surface area of the support member 240c is sufficient to support the pressed dough ball 244 in conjunction with one or more additional support members but is insufficient to support the incorrectly formed ball of dough 246 alone.

In some implementations, some or all of the transfer system 200 is replaced or exchanged when a new recipe is selected for the production line. For example, the oven removal conveyor 228 and the banded oven discharge 230 are removed from the transfer system 200 and another oven removal conveyor and banded oven discharge are placed in the transfer system (e.g., where the replacement banded oven discharge is configured for the five axes corresponding to the new recipe).

In some implementations, the drive roller 236 and/or the passive roller 238 include a plurality of the grooves 242a-b such that there is not a one to one correlation between the support members 240a-e and the grooves 242a-b. For example, the drive roller 236 includes two grooves 256a-b adjacent to the groove 242a, with one groove on either side of the groove 242a. While the production line is processing a recipe, the support member 240c can be moved to either of the adjacent grooves 256a-b to improve processing of the pressed dough balls 108.

Continuing the example, when the edge of a pressed dough ball is close to the edge of the support member 240c, the pressed dough ball may become stuck between the support member 240c and the drive roller 236. To reduce the possibility of a jam, the support member 240c can be moved to the groove adjacent the groove 242a where positioning of the support member 240c in the adjacent groove reduces the distance between the adjacent support members that the pressed dough ball is supported by.

In another example, the drive roller 236 includes a plurality of grooves along the entire length of the drive roller 236. For example, each of the grooves is adjacent to two other grooves with the exception of the two grooves on either end of the drive roller 236. Including grooves along the entire length of the drive roller 236 and/or the passive roller 238 allows the support members 240a-e to be moved to different positions along the rollers depending on the process recipe used by the production line.

For example, the location of the support members 240a-e can be adjusted during processing to reduce the chance that one of the pressed dough balls 108 will be caught in the banded oven discharge 230. Additionally, when the recipe used by the production line is changed, the position of the support members 240a-e can be altered without replacing the banded oven discharge 230 with a banded oven discharge with another configuration.

When the banded oven discharge 230 includes a plurality of the grooves 242a-b such that there is not a one to one correspondence between the grooves 242a-b and the support members 240a-e, the support members 240a-e can be manually moved between adjacent grooves depending on the desired recipe parameters or operating conditions. Alternatively, the banded oven discharge 230 includes an automated system (e.g., a robot) that moves the support members 240a-e between adjacent grooves. In this implementation, the banded oven discharge 230 includes a holding area (not shown) where support members are positioned when not in use (e.g., at one or both ends of the driver roller 236 and the passive roller 238).

The distance between adjacent grooves is selected so that the support members 240a-e do not move between the adjacent grooves without interaction with the transfer system 200 and so that the support members 240a-e can be easily moved when required for a recipe or by an operator. For example, one of the support members 240a-e moves to an adjacent groove when an operator physically moves the support member and does not move between grooves otherwise. In another example, a support member moves between adjacent grooves when a robot or automated system moves the support member to the adjacent groove.

In one example, the distance between adjacent grooves is proportional to the width of the support members 240a-e. In certain implementations, the distance between adjacent grooves is zero. For example, when one groove ends, another groove begins at the ending point. In this example, the edges of the grooves are rounded to reduce the possibility of damage to the support members 240a-e when a support member is moved between adjacent grooves.

In some implementations, the distance between adjacent grooves is selected to minimize the possibility of a support member moving between adjacent grooves without system interaction. For example, the distance between adjacent grooves is selected so that it is unlikely for a support member to move between grooves without interaction with an operator or another part of the transfer system 200.

In various implementations, the banded oven discharge 230 is located between the cooling rack input conveyor 234 and a cooler (e.g., the cooler 100d). The location of the banded oven discharge 230 is selected based on the layout of the production line and the types of tools included in the production line.

In certain implementations, an oven removal system 250, shown in FIG. 2E, includes a plurality of rollers 252a-f, which drive the oven removal conveyor 228. The rollers 252a-f move the oven removal conveyor 228 in a longitudinal direction along the longitudinal axes B1-3.

Each of the rollers 252a-f is positioned along one of the longitudinal axes B1-3 to support balls of dough that move along the path defined by the longitudinal axes B1-3. For example, as the pressed dough ball 244 moves along the longitudinal axis B2, the roller 252b and the roller 252e support the pressed dough ball 244. Similarly, as the incorrectly formed ball of dough 246 moves along the longitudinal axis B1, the roller 252c and the roller 252f support the incorrectly formed ball of dough 246.

Alternatively, some of the rollers 252a-f are located in the oven removal system 250 along a longitudinal axes that does not correspond with a path traveled by one of the pressed dough balls 108. For example, when the production line is initially configured for three longitudinal axes and later reconfigured for a recipe with five longitudinal axes, some of the rollers 252a-f may not lie on an axis defined by one of the five longitudinal axes associated with the new recipe.

In some implementations, each of the rollers 252a-f comprises double rollers to support the oven removal conveyor 228.

The rollers 252a-f are connected to a motor 254. The motor 254 rotates the rollers 252a-f while the production line processes the pressed dough balls 108 (e.g., the pressed dough ball 244). As the rollers 252a-f rotate, the rollers 252a-f drive the oven removal conveyor 228, which transfers the pressed dough ball 244 to the banded oven discharge 230.

Figure 3:
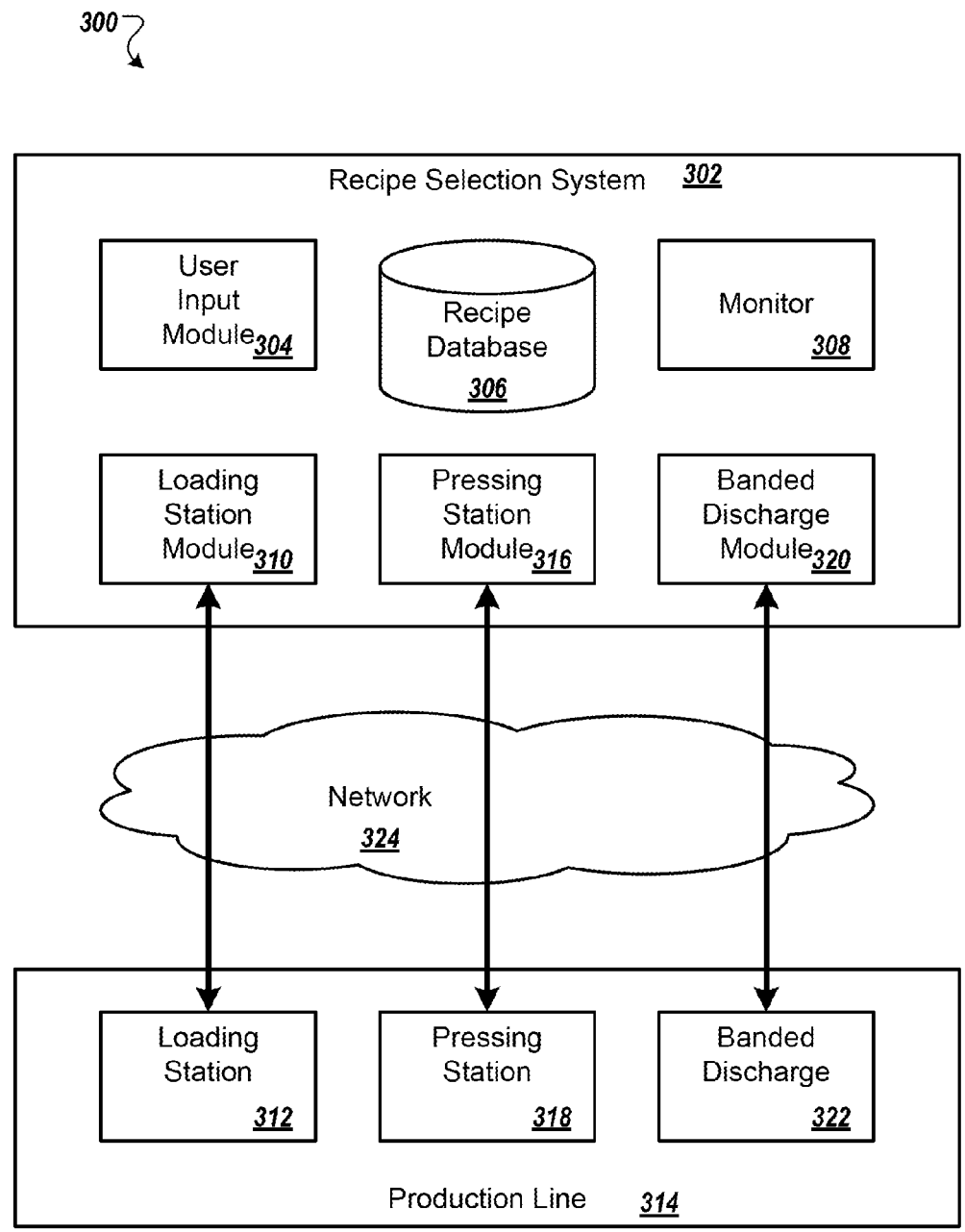
FIG. 3 illustrates an example of a system for selecting a production line process recipe.

FIG. 3 illustrates an example of a system 300 for selecting a production line recipe. The system 300 includes a recipe selection system 302, which receives user input and identifies parameters associated with a selected recipe.

For example, the recipe selection system 302 includes a user input module 304 that receives input from a user. The input can be selection of a recipe from a recipe database 306. Alternatively, a user can directly input a recipe into the recipe selection system 302 into a user interface associated with user specified recipes.

A monitor 308, included in the recipe selection system 302, presents information to a user. For example, the monitor 308 displays a user interface that allows a user to enter recipe information into the recipe selection system 302 or select a recipe from the recipe database 306.

The monitor 308 can display confirmation information that verifies a recipe selection or recipe information entered by the user. For example, the user input module 304 receives user input identifying a recipe, the recipe selection system 302 validates the recipe to ensure that the recipe parameters are acceptable, and the monitor 308 presents a recipe confirmation to the user.

A loading station module 310, included in the recipe selection system 302, identifies the recipe parameters associated with a loading station 312 included in a production line 314. For example, the loading station module 310 determines the pattern of dough balls used by the recipe.

In some implementations, the loading station module 310 determines if the loading station positioned in the production line is configured for the recipe. For example, the loading station module 310 determines that a 3×3 pattern of dough balls is required by the selected recipe and that the production line is currently setup for a 4×3 pattern of dough balls. The loading station module 310 can provide a message (e.g., on the monitor 308) to an operator of the production line indicating that the loading station 312 should be configured for a 3×3 pattern of dough balls.

Alternatively, the loading station module 310 provides the production line 314 with information indicating that the loading station 312 should be reconfigured. For example, the production line 314 receives the information from the loading station module 310 and identifies a 3×3 dough ball loader to place on the loading station 312. The production line automatically removes the 4×3 dough ball loader from the loading station 312 and attaches the 3×3 dough ball loader onto the loading station 312 without user or operator interaction.

A pressing station module 316, included in the recipe selection system 302, configures a pressing station 318 (e.g., the pressing station 106) in the production line 314. For example, the pressing station module 316 identifies the pattern of dough balls specified by the selected recipe and determines the configuration for the pressing station 318.

In certain implementations, the production line 314 receives information from the pressing station module 316 that identifies the configuration for the pressing station 318. For example, the configuration includes adjustments and/or changes the production line 314 automatically makes to the pressing station 318 for the selected recipe.

In one example, the production line 314 replaces a skin attached to a pressing platen in the pressing station 318. In another example, the production line 314 (or a controller in the production line 314) adjusts the pressure used at the pressing station 318 when forming pressed dough balls. In this example, the pressure of the pressing station 318 is adjusted for the press cycle associated with the selected recipe to increase the uniformity of the pressed dough balls.

A banded discharge module 320, included in the recipe selection system 302, identifies one or more adjustments for a banded discharge 322 based on the selected recipe. For example, the banded discharge module 320 determines that a recipe parameter identifies five longitudinal axes and the banded discharge 322 is configured for three longitudinal axes. In this example, the banded discharge module 320 notifies an operator of the required change. The notification can include identification of the distance between adjacent transfer belts and/or the recommended location of the transfer belts in the banded discharge 322.

In some implementations, the production line 314 automatically adjusts the banded discharge 322 based on parameter adjustments identified by the banded discharge module 320. For example, the production line 314 automatically moves one or more support members to align with the five longitudinal axes specified by the selected recipe. In one example, the production line 314 places two support members equidistant from each of the five longitudinal axes. In this example, the support members are placed about 3 inches or less from the associated longitudinal axis.

In certain implementations, when the recipe used by the production line 314 changes, the banded discharge module 320 determines that the banded discharge 322 does not need any configuration changes. For example, when the banded discharge 322 is configured for a 3×3 press cycle (with three longitudinal columns of dough balls) and a selected recipe requires a 3×4 press cycle (with three longitudinal columns and four latitudinal rows of dough balls), the locations of the support members in the banded discharge 322 do not need to be adjusted.

In various implementations, the banded discharge module 320 receives notifications from the banded discharge 322. For example, when a rejected product cart is full and needs be removed from the production line 314 the production line 314 provides the banded discharge module 320 with a cart removal notification. Upon receiving the cart removal notification, the banded discharge module 320 presents a message on the monitor 308 to an operator indicating that the rejected product cart should be exchanged.

The recipe selection system 302 communicates with the production line 314 through a network 324. For example, the network 324 is a local area network at a production facility that allows a remote user to monitor the production facility. In another example, the network 324 connects separate stations in the production line 314 with the recipe selection system 302 and does not allow remote access to the production line 314 or the recipe selection system 302.

Figure 4:
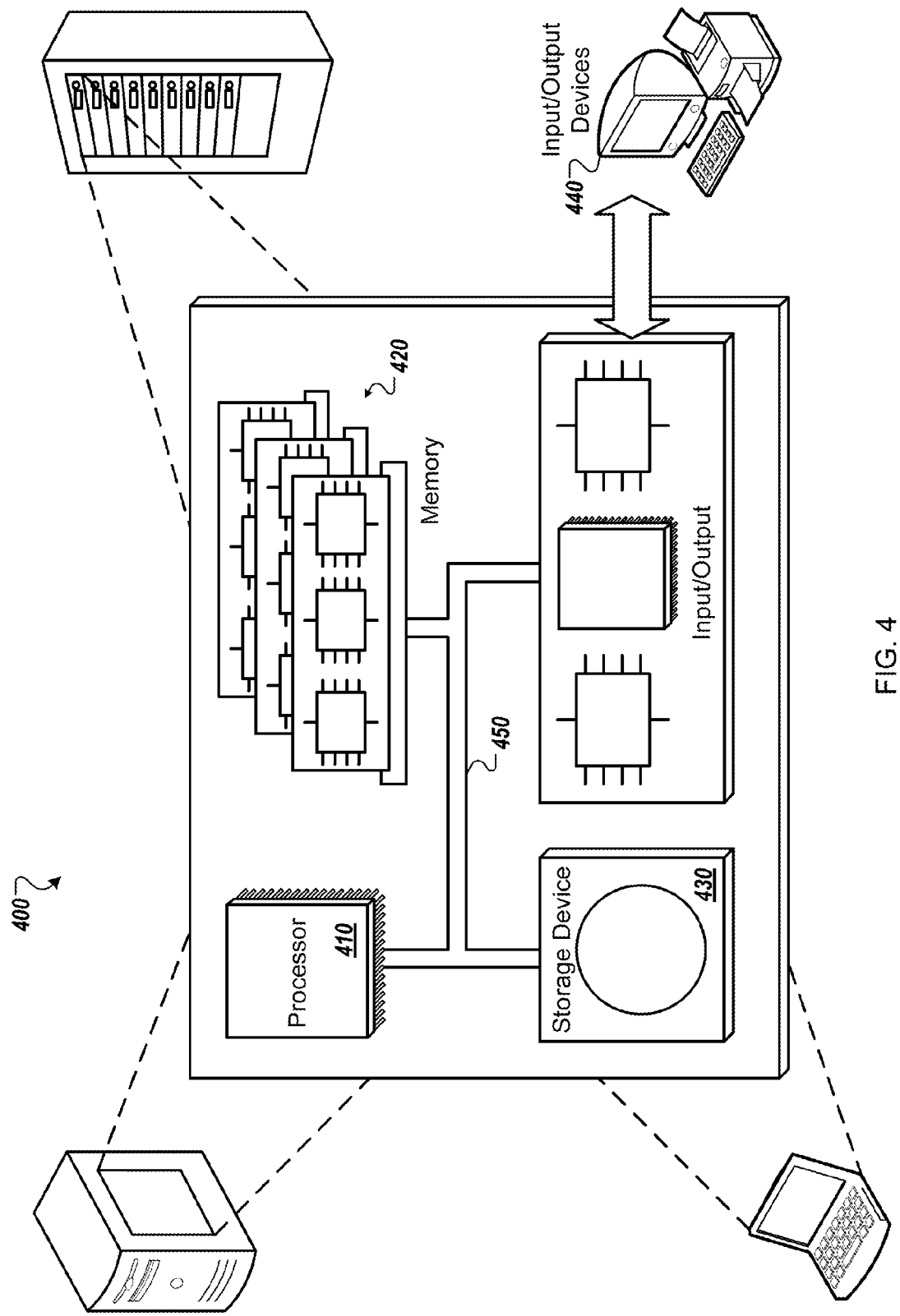
FIG. 4 is a block diagram of a computing system optionally used in connection with computer-implemented methods described in this document.

FIG. 4 is a schematic diagram of a generic computer system 400. The system 400 is optionally used for the operations described in association with any of the computer-implemented methods described previously, according to one implementation. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 is optionally a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

In some examples, the features described are implemented in digital electronic circuitry, or in computer hardware, firmware, software, or in combinations of them. The apparatus is optionally implemented in a computer program product tangibly embodied in an information carrier, e.g., in a machine-readable storage device or in a propagated signal, for execution by a programmable processor; and method steps are performed by a programmable processor executing a program of instructions to perform functions of the described implementations by operating on input data and generating output. The described features are optionally implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that are optionally used, directly or indirectly, in a computer to perform a certain activity or bring about a certain result. A computer program is optionally written in any form of programming language, including compiled or interpreted languages, and it is deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory are optionally supplemented by, or incorporated in, ASICs (application-specific integrated circuits).

To provide for interaction with a user, the features in some instances are implemented on a computer having a display device such as a CRT (cathode ray tube) or LCD (liquid crystal display) monitor for displaying information to the user and a keyboard and a pointing device such as a mouse or a trackball by which the user provides input to the computer.

The features are optionally implemented in a computer system that includes a back-end component, such as a data server, or that includes a middleware component, such as an application server or an Internet server, or that includes a front-end component, such as a client computer having a graphical user interface or an Internet browser, or any combination of them. The components of the system are connected by any form or medium of digital data communication such as a communication network. Examples of communication networks include, e.g., a LAN, a WAN, and the computers and networks forming the Internet.

The computer system optionally includes clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications are optionally made without departing from the spirit and scope of this disclosure. Accordingly, other embodiments are within the scope of the following claims.

What is claimed is:

1. A method comprising:
   receiving, at a first conveyor in a production line, a plurality of comestibles, the first conveyor comprising a first roller, a second roller spaced apart from the first roller, and two adjacent support members that each couple with the first roller and the second roller and are a predetermined distance apart;
   translating, by a motor, the first roller to move the two adjacent support members;
   transferring, by the two adjacent support members, during translation of the first roller, a first pressed comestible from the first conveyor to a second conveyor separate from the first conveyor, the second conveyor included in the production line, the first pressed comestible having a first diameter substantially greater than the predetermined distance between the two adjacent support members; and
   rejecting, by the two adjacent support members, a second comestible different from the first comestible, the second comestible having a second diameter about the same as or less than the predetermined distance between the two adjacent support members, the plurality of comestibles including the first pressed comestible and the second comestible.

2. The method of claim 1, further comprising adjusting the predetermined distance between the two adjacent support members.

3. The method of claim 1, further comprising:
   selecting a recipe for the production line, the recipe including a desired diameter for the plurality of comestibles;
   determining the predetermined distance between the two adjacent support members using the recipe; and
   adjusting a distance between the two adjacent support members to the predetermined distance.

4. The method of claim 3, further comprising:
   adjusting a longitudinal distance between the first roller and the second roller based on the recipe selected for the production line, wherein the longitudinal distance is less than the desired diameter for the plurality of comestibles.

5. The method of claim 4, wherein the longitudinal distance is at most about 2 inches less than the desired diameter.

6. The method of claim 4, wherein the longitudinal distance is at most about 1.5 inches less than the desired diameter.

7. The method of claim 3, wherein the predetermined distance is between about 1 to about 6 inches.

8. The method of claim 1, wherein the rejecting comprises removing the second comestible from the production line.

9. The method of claim 8, further comprising:
   placing a plurality of dough balls on a third conveyor according to a press cycle layout, the plurality of dough balls including a first subset of dough balls;
   pressing, at a pressing station, the first subset of dough balls to form a first subset of comestibles including pressing a first dough ball from the first subset of dough balls to form the first pressed comestible with the first diameter, wherein receiving the plurality of comestibles comprises transferring the first subset of comestibles from the third conveyor to the first conveyor, the plurality of comestibles comprising the first subset of comestibles.

10. The method of claim 9, further comprising cooling, by a cooler, the first pressed comestible after transferring the first pressed comestible to the second conveyor.

11. The method of claim 10, further comprising baking, by an oven, the first pressed comestible before transferring the first pressed comestible to the second conveyor.

12. The method of claim 9, further comprising moving, by a third conveyor, the second comestible away from the first conveyor after the rejecting.

13. The method of claim 9, wherein placing the plurality of dough balls on the third conveyor comprises placing a second dough ball on the third conveyor, and the second comestible comprises the second dough ball.

14. The method of claim 13, wherein the pressing station does not press the second dough ball.

15. The method of claim 9, further comprising:
   determining the predetermined distance between the two adjacent support members using a predetermined thickness of a comestible, wherein each of the plurality of comestibles has a thickness inversely proportional to a diameter of the comestible and the thickness is determined by an amount the comestible was pressed.

16. The method of claim 9, wherein the pressing station does not complete a pressing process of the second comestible.

17. The method of claim 1, wherein:
   the first conveyor receives the plurality of comestibles in a longitudinal direction;
   the second roller is spaced apart longitudinally from the first roller;
   the two adjacent support members are a predetermined distance apart in a latitudinal direction; and
   the motor translates the first roller to move the two adjacent support members in the longitudinal direction.

18. The method of claim 17, wherein the two adjacent support members are parallel.

19. The method of claim 17, wherein the longitudinal direction is orthogonal to the latitudinal direction.

20. The method of claim 1, further comprising:
   adjusting the two adjacent support members so that a center axis of an aperture defined by the two adjacent support members approximately aligns with an axis defined by a press cycle layout.

* * * * *